(12) United States Patent
Treace

(10) Patent No.: US 7,066,942 B2
(45) Date of Patent: Jun. 27, 2006

(54) BENDABLE NEEDLE FOR DELIVERING BONE GRAFT MATERIAL AND METHOD OF USE

(75) Inventor: John T. Treace, Germantown, TN (US)

(73) Assignee: Wright Medical Technology, Inc., Arlington, TN (US)

(*) Notice: Subject to any disclaimer, the term of this patent is extended or adjusted under 35 U.S.C. 154(b) by 204 days.

(21) Appl. No.: 10/679,077

(22) Filed: Oct. 3, 2003

(65) Prior Publication Data
US 2004/0068264 A1   Apr. 8, 2004

(51) Int. Cl.
  *A61B 17/58*   (2006.01)
  *A61F 2/00*    (2006.01)
(52) U.S. Cl. .................................................. 606/92
(58) Field of Classification Search .................. 606/53, 606/86, 92, 93, 94; 604/134, 135, 152, 154, 604/155, 97.01, 97.02, 97.03, 187–189, 218, 604/224, 227; 433/89, 90
See application file for complete search history.

(56) References Cited

U.S. PATENT DOCUMENTS

| | | | |
|---|---|---|---|
| 5,800,409 A * | 9/1998 | Bruce | 604/523 |
| 5,824,087 A * | 10/1998 | Aspden et al. | 606/94 |
| 6,241,734 B1 * | 6/2001 | Scribner et al. | 606/93 |
| 6,248,110 B1 * | 6/2001 | Reiley et al. | 606/93 |
| 6,575,919 B1 * | 6/2003 | Reiley et al. | 600/567 |
| 6,579,291 B1 * | 6/2003 | Keith et al. | 606/61 |
| 6,592,559 B1 * | 7/2003 | Pakter et al. | 604/272 |
| 6,716,216 B1 * | 4/2004 | Boucher et al. | 606/86 |
| 6,740,093 B1 * | 5/2004 | Hochschuler et al. | 606/94 |
| 6,805,695 B1 * | 10/2004 | Keith et al. | 606/61 |
| 6,899,716 B1 * | 5/2005 | Cragg | 606/86 |

\* cited by examiner

*Primary Examiner*—Eduardo C. Robert
*Assistant Examiner*—Anu Ramana (57) ABSTRACT

A bone graft needle, particularly useful in minimally invasive procedures, is provided. The bone graft needle as well as its corresponding penetrating member may be made from bendable materials so that the combined instrument can more easily access hard to reach areas of the body.

10 Claims, 6 Drawing Sheets

FIG. 10

BENDABLE NEEDLE FOR DELIVERING BONE GRAFT MATERIAL AND METHOD OF USE

RELATED APPLICATIONS

This application is related to Assignee's co-pending U.S. patent application Ser. No. 10/678,701, filed the same day as this patent application.

BACKGROUND OF THE INVENTION

1. Field of the Invention

The present invention generally pertains to the use of graft materials for promoting bone growth and, more particularly, to ported needles for delivering bone graft materials to metaphyseal compression fractures, other bone voids or other bone defect areas.

2. Discussion of the Prior Art

In the past, bone graft materials have been delivered to bone defect areas, such as metaphyseal compression fractures or bone voids as well as other areas of bone structures having discontinuities, cavities, recesses or the like (hereinafter referred to as bone defect areas). Minimally invasive bone graft procedures are preferred in many cases, and the delivery or injection of bone graft material to the bone defect areas has been accomplished using a needle having an open distal end forming an axial port for delivering the bone graft material to the bone defect areas from a syringe coupled with the proximal end of the needle. Such needles have been unable to be precisely positioned, such as by bending. Therefore, they have not been useful for ejecting bone graft towards hard to reach locations in the body. Accordingly, there is room for improvement within the art.

SUMMARY OF THE INVENTION

Accordingly, it is an object of the present invention to overcome the above mentioned disadvantages of the prior art by providing a bendable bone graft needle particularly useful in minimally invasive procedures. Another object of the present invention is to deliver bone graft material to a bone defect area by extruding the bone graft material through a bendable needle.

The present invention is further generally characterized in a method of delivering bone graft material to a bone defect area including the steps of providing an instrument for preparing said location for said receiving bone graft material, the instrument comprising: a bone graft needle for delivery of bone graft material to a bone defect area in a patient's body, the needle comprising: an elongate bendable tubular delivery member having an open distal end for positioning at the bone defect area via a minimally invasive portal providing access to the bone defect area from externally of the patient's body and having an open proximal end for being supplied with bone graft material from externally of the patient's body, the open distal end being aligned with a central longitudinal axis of the delivery member for discharge of the bone graft material therefrom towards the bone defect area; and an elongate flexible penetrating member for receipt within the bone graft needle.

BRIEF DESCRIPTION OF THE DRAWINGS

Other objects and advantages of the present invention will become apparent from the following description of the preferred embodiments taken in conjunction with the accompanying drawings, wherein like parts in each of the several figures are identified by the same reference characters.

DESCRIPTION OF THE PREFERRED EMBODIMENTS

Figure 1:
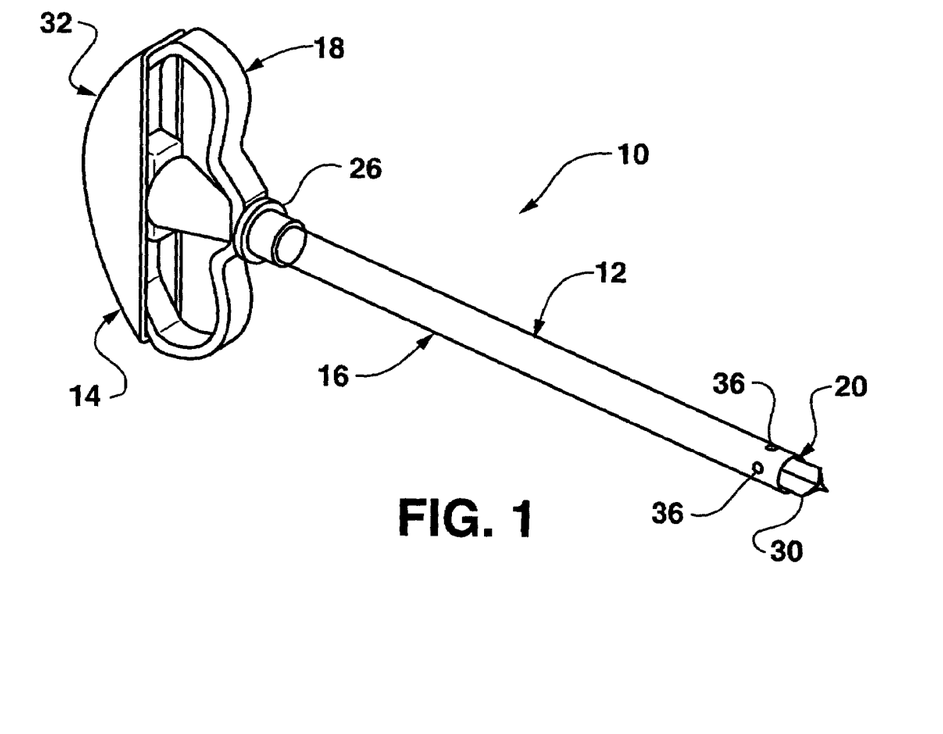
FIG. 1 is a perspective view of an instrument assembly incorporating a bone graft needle according to the present invention.
Figure 2:
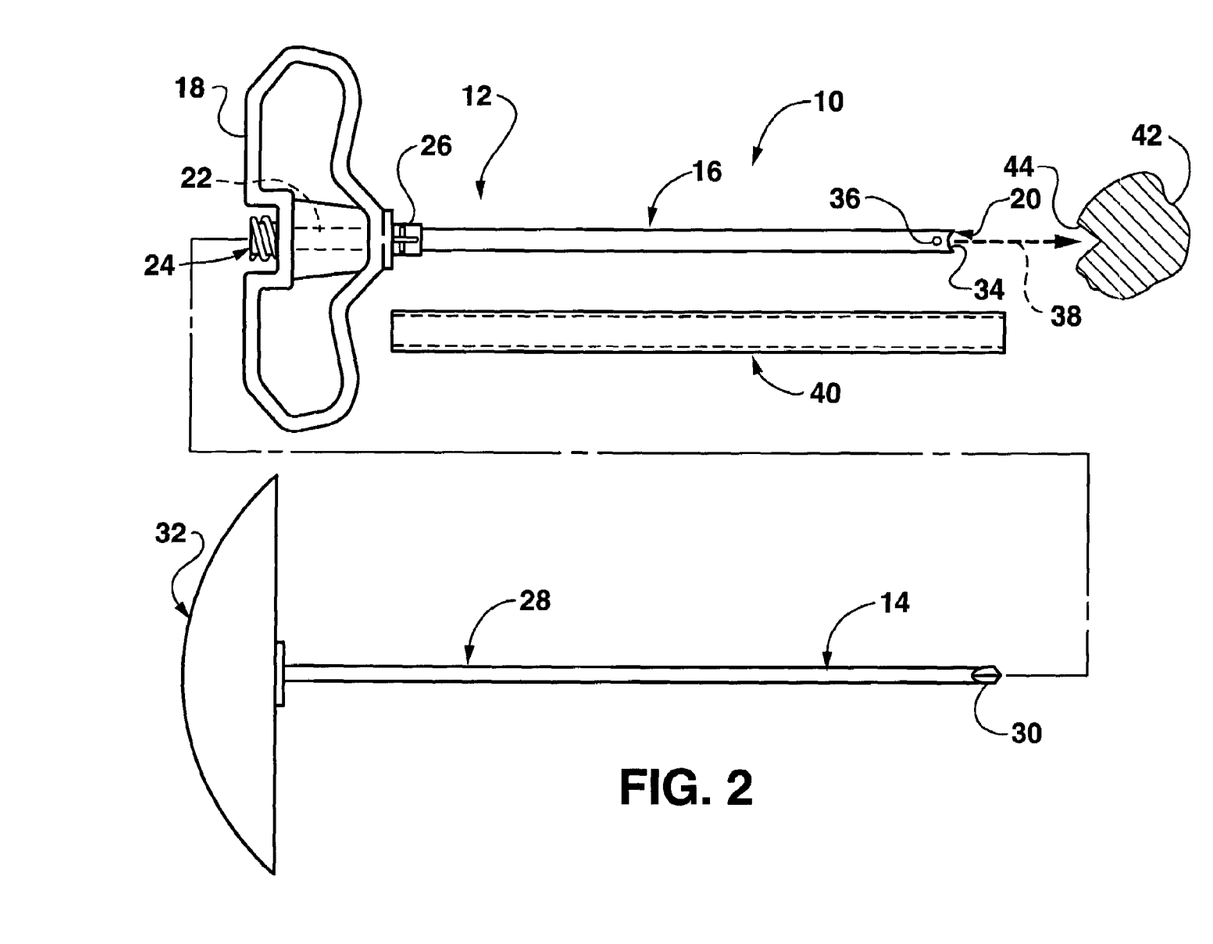
FIG. 2 is an exploded side view of the instrument assembly including a side view of the bone graft needle of the present invention.

The present invention relates to a bone graft needle used to deliver bone graft material to a bone defect area in a patient's body in a minimally invasive procedure in which the bone defect area is accessed via a minimal portal or incision. FIGS. 1 and 2 illustrate an instrument assembly 10 comprising a bone graft needle 12 and a penetrating member 14, such as a trocar. The bone graft needle 12 comprises an elongate tubular delivery member 16 extending distally from a handle 18. The delivery member 16 has an open distal end 20 communicating with a longitudinal passage 22 extending entirely through the delivery member 16 and the handle 18. A hollow coupling 24 having open distal and proximal ends is disposed at a proximal end of passage 22 with the interior of the coupling 24 in communication with the passage 22. The coupling 24 is designed for releasable attachment to a standard syringe and may be designed as a conventional luer lock coupling. The handle 18 can have various configurations to facilitate grasping. A proximal end of the delivery member 16 can be attached to the handle 18 via a hub 26 or in any desired manner. The proximal end of the delivery member 16 can extend any desired distance into a passage of the handle 18 or can extend entirely through the handle. The coupling 24 can be attached to the handle 18 in various ways or may be formed integrally, unitarily with the handle. The distal end of the coupling 24 can extend any desired amount into the passage of the handle 18. Accordingly, it should be appreciated that the longitudinal passage 22 can be formed in its entirety by the lumen of delivery member 16, can be formed in part by the lumen of the delivery member 16 and by a passage in handle 18, or can be formed in part by the lumen of delivery member 16, a passage in the handle 18 and the interior of the coupling 24.

Figure 3:
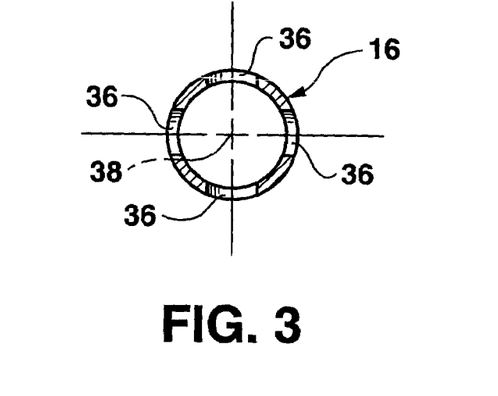
FIG. 3 is a sectional view of a delivery member of the bone graft needle taken along line A—A of FIG. 2.

The delivery member 16, as best shown in FIGS. 2 and 3, has an external cross sectional diameter or size for insertion through a minimally invasive portal or incision formed in the patient's body to access a bone defect area. The delivery member 16 has an internal cross-sectional diameter or size to receive the penetrating member 14 therethrough. As shown in FIGS. 1 and 2, the penetrating member 14 includes an elongate shaft 28 having a tissue penetrating distal end 30 and having a proximal end attached to a hub 32. The shaft 28 is insertable in the passage 22 extending entirely through the bone graft needle and, when the hub 32 is in abutment with the handle 18, the tissue penetrating distal end 30 protrudes distally from the open distal end 20 of the delivery member 16 as shown in FIG. 1. The instrument assembly 10 formed when the penetrating member 14 is inserted in the delivery member 16 can be utilized to form a minimally invasive portal in anatomical tissue of a patient to establish access to a bone defect area. The exposed tissue penetrating distal end 30 of the penetrating member is used to penetrate the anatomical tissue to introduce the distal end 20 of delivery member 16 at or near the bone defect area. Thereafter, the penetrating member 14 can be removed from the bone graft needle 12 leaving the bone graft needle in place to maintain the thusly formed portal with the handle 18 disposed externally of the patient's body. It should be appreciated, however, that the bone graft needle 12 can be used independently of a penetrating member and that the bone graft needle can be introduced at or near a bone defect area via a pre-established portal.

The open distal end 20 of delivery member 16 is circumscribed by a circumferential edge 34 that is provided with one or more proximally curving indentations as best shown in FIG. 2. Accordingly, the circumferential edge 34 comprises one or more distal most edge segments or points and one or more proximal most edge segments or points spaced proximally from the one or more distal most edge segments or points. A plurality of radial ports or openings 36 are formed through delivery member 16 proximally of circumferential edge 34. As shown in FIG. 3, four radial ports 36 are formed through the wall of delivery member 16 at spaced locations about a central longitudinal axis 38 of delivery member 16. The ports 36 are shown as being equally spaced about the central longitudinal axis 38 at 90 degree spaced locations about the central longitudinal axis 38. It should be appreciated, however, that the ports 36 can be equally spaced or variably spaced about the central longitudinal axis. The ports 36 are shown as having a circular perimetrical configuration, but the ports can have other perimetrical configurations including oval, elliptical and various longitudinally elongated perimetrical configurations. Each port 36 has a longitudinal dimension in a direction parallel to the central longitudinal axis 38. In the case of ports 36, the longitudinal dimension corresponds to the diameter of the ports. Each port 36 begins a distance D proximally of the proximal most edge segment or point of circumferential edge 34 as shown in FIG. 2. Where the circumferential edge is disposed in its entirety in a plane perpendicular to the central longitudinal axis 38, the proximal most edge segment or point will be disposed in the plane perpendicular to the central longitudinal axis 38 as described below for FIGS. 6 and 7. Distance D may be in the range of 0.020 inch to 0.275 inch. For delivery member 16 having ports 36 that are 0.063 inch in diameter, the longitudinal dimension for ports 36 is also 0.063 inch and a preferred range for distance D is 0.0505 inch to 0.0805 inch. FIG. 2 illustrates a removable tubular sheath 40 that may be disposed over the delivery member 16 prior to use.

In a preferred embodiment for bone graft needle 12, the needle is a 4 inch needle with delivery member 16 made of 304 stainless steel or other rigid biocompatible material and having a J-type cannulated distal end or tip; the delivery member is 0.185 inch in diameter; the radial ports 36 are 0.063 inch in diameter with centers at 90° (+or −2.0°) spaced locations about the central longitudinal axis; and the centers of ports 36 are located 0.082 inch (+0.030 inch, −0.000 inch) proximally of the proximal most edge segment or point of circumferential edge 34. The needle 12 may be a JAMSHIDI-type needle with a luer-lock coupling or connector.

The open distal end 20 defines an axial or longitudinal port for delivery member 16 from which a bone graft material is discharged from delivery member 16 in an axial or longitudinal direction. The radial ports 36 permit bone graft material to be discharged from delivery member 16 in a direction radial to the central longitudinal axis 38 so that bone graft material is discharged radially simultaneously with the axial discharge.

In a method according to the present invention, the distal end 20 of delivery member 16 is introduced at or near a bone defect area in a patient's body via a minimally invasive portal providing access to the bone defect area from externally of the patient's body. As discussed above, the bone graft needle 12 may be assembled with a penetrating member to form an instrument assembly that may be used to form the portal. Visualization of the bone defect area may be accomplished using a remote viewing device, such as a fluoroscope or x-ray device, as conventionally utilized in minimally invasive procedures. FIG. 2 illustrates a bone segment 42 having a bone defect area 44 to be supplied with a bone graft material delivered via the bone graft needle 12. The bone defect area 44 may include metaphyseal compression fractures, bone voids, discontinuities, cavities, recesses, non-unions or the like. The bone graft material to be delivered to the bone defect area may be any synthetic or tissue-based material that promotes bone growth and may be provided in paste form. Representative bone graft materials include calcium sulfate, as represented by the OSTEOSET® bone graft substitute of Wright Medical Technology, Inc., Allomatrix® and MIIG™ 115 of Wright Medical Technology, Inc., and demineralized bone matrix. The bone graft material is supplied to the bone graft needle 12 via a conventional syringe coupled with the coupling 24. With the handle 18 disposed externally of the patient's body, the syringe containing the bone graft material is coupled with coupling 24. The distal end 20 of delivery member 16 is positioned at or adjacent the bone defect area 44 and, depending on the size of the bone defect area, the distal end 20 may be positioned within the bone defect area. With the distal end 20 properly positioned, a plunger of the syringe is depressed to fill the passage 22 with the bone graft material. Depressing the plunger of the syringe pressurizes the bone graft material in passage 22 causing the bone graft material to be simultaneously discharged axially through distal end 20 and radially through the ports 36 to fill the bone defect area 44. In the case of delivery member 16, the bone graft material is discharged simultaneously in five directions, i.e. in a first direction axially or longitudinally through distal end 20 and in second, third, fourth and fifth radial directions through ports 36, respectively. In the event that the distal end 20 is in abutment with bone or other anatomical tissue, plugging or clogging of the delivery member 16 is avoided since discharge of the bone graft material continues through ports 36. In addition, back pressure is reduced for easier injection of the bone graft material since resistance to injection is reduced due to the multi-directional discharge provided by opening 20 and ports 36. The arrangement of ports 36 along the circumference of delivery member 16 permits radial discharge and distribution of the bone graft material and allows the bone defect area to be filled radially as well as from the distal end 20 of the delivery member. The distribution of ports 36 along the circumference of the delivery member allows the bone defect area to be filled in a range of 360 degrees around the delivery member. Also, the circumferential distribution of the ports 36 provides a more even and more balanced distribution of bone graft material to the bone defect area. Once the bone defect area 44 has been sufficiently supplied or filled with the bone graft material, the needle 12 is removed from the patient's body through the portal. The bone graft material remains in the patient's body to promote bone growth or regeneration.

Figure 4:
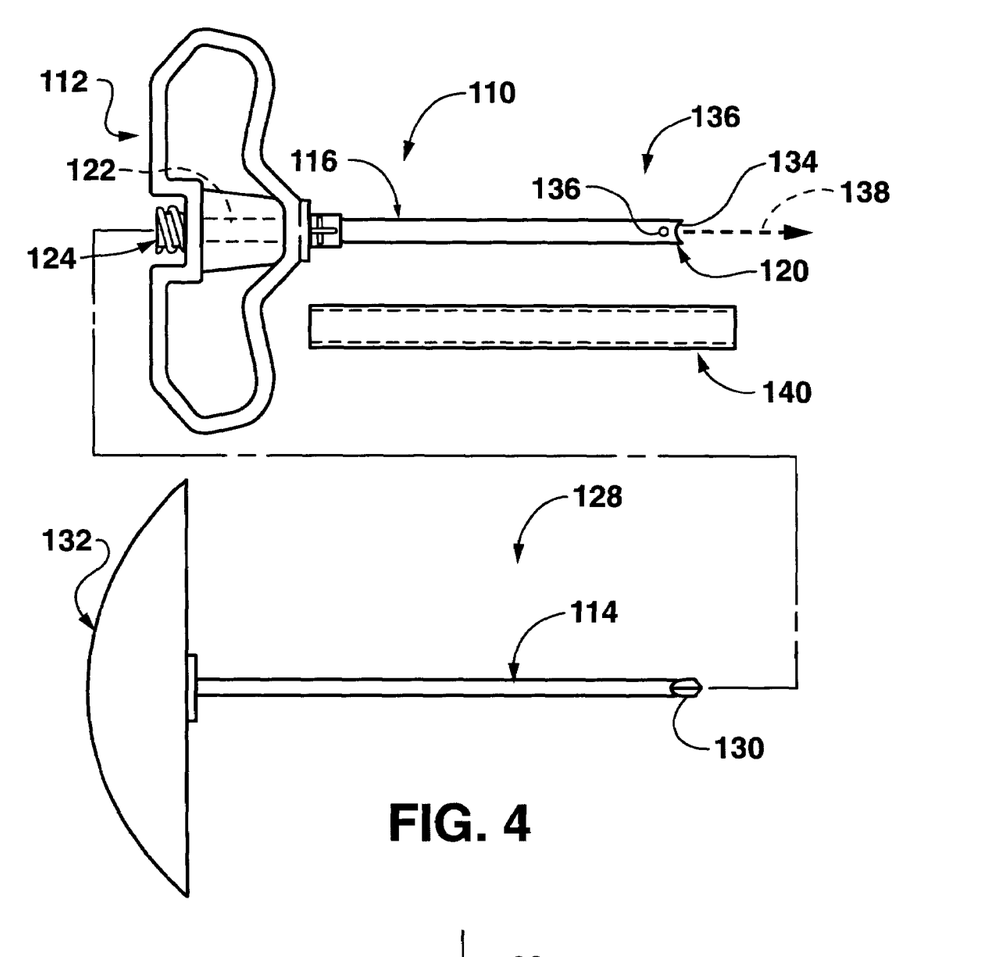
FIG. 4 is an exploded side view of an alternative instrument assembly incorporating an alternative bone graft needle according to the present invention.

FIG. 4 illustrates an alternative instrument assembly 110 comprising a bone graft needle 112 and a penetrating member 114. The instrument assembly 110 is similar to instrument assembly 10 except that the bone graft needle 112 and the penetrating member 114 are shorter in length than the bone graft needle 12 and penetrating member 14. Accordingly, it should be appreciated that the bone graft needle, as well as the penetrating member, can be provided in different lengths depending on the length needed to access the bone defect area. The bone graft needle 112 also differs from the bone graft needle 12 in that the delivery member 116 is of smaller external diameter than the delivery member 16. It should be appreciated, therefore, that the delivery members of the bone graft needles can be provided in various diametric sizes. Of course, the shafts of the penetrating members can also be provided in various diametric sizes depending on the anatomical tissue to be penetrated. The radial ports 136 for delivery member 116 differ from the ports 36 in that the ports 136 are smaller in diameter.

Figure 5:
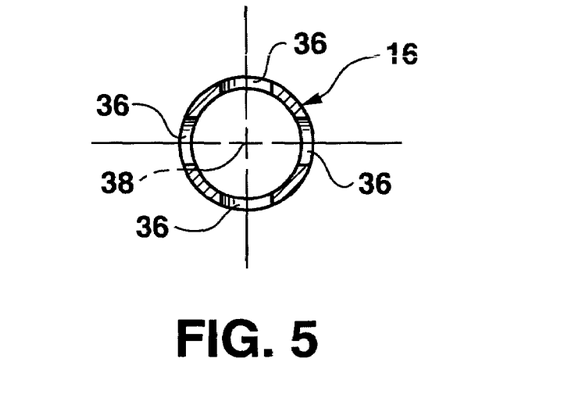
FIG. 5 is a sectional view of the delivery member of the alternative bone graft needle taken along lines B—B of FIG. 4.

In a preferred embodiment for bone graft needle 112, the external diameter of delivery member 116 is 0.115 inch; the ports 136 have a diameter of 0.047 inch with centers at 90° (+or −2.0°) spaced locations about the central longitudinal axis 138; distance D may be in the range of 0.020 inch to 0.275 inch and is preferably in the range of 0.082 inch to 0.112 inch; the needle 112 is a 6 cm needle with delivery member 116 made of 304 stainless steel or other rigid biocompatible material and having a J-type cannulated distal end or tip; and the centers of ports 136 are located 0.082 (+0.030 inch, −0.000 inch) proximally of the proximal most edge segment or point of circumferential edge 134. The needle 112 may be a JAMSHIDI-type needle with a luer-lock coupling or connector.

Figure 6:
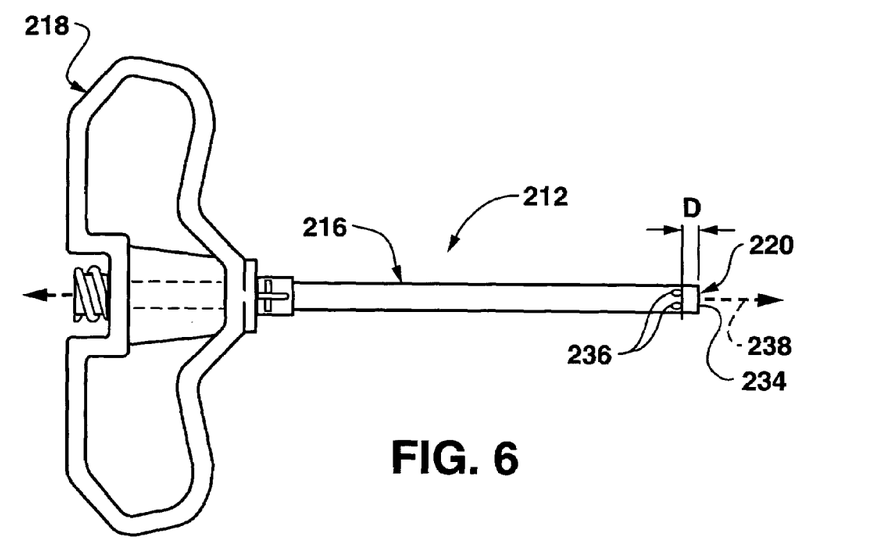
FIG. 6 is a side view of another alternative bone graft needle according to the present invention.

FIG. 6 is illustrative of a bone graft needle 212 in which the delivery member 216 has a distal end 220 with a circumferential edge 234 disposed in a plane perpendicular to the central longitudinal axis 238. Distance D for delivery member 216 is defined from the plane of edge 234 to where the ports 236 begin proximally of edge 234.

Figure 7:
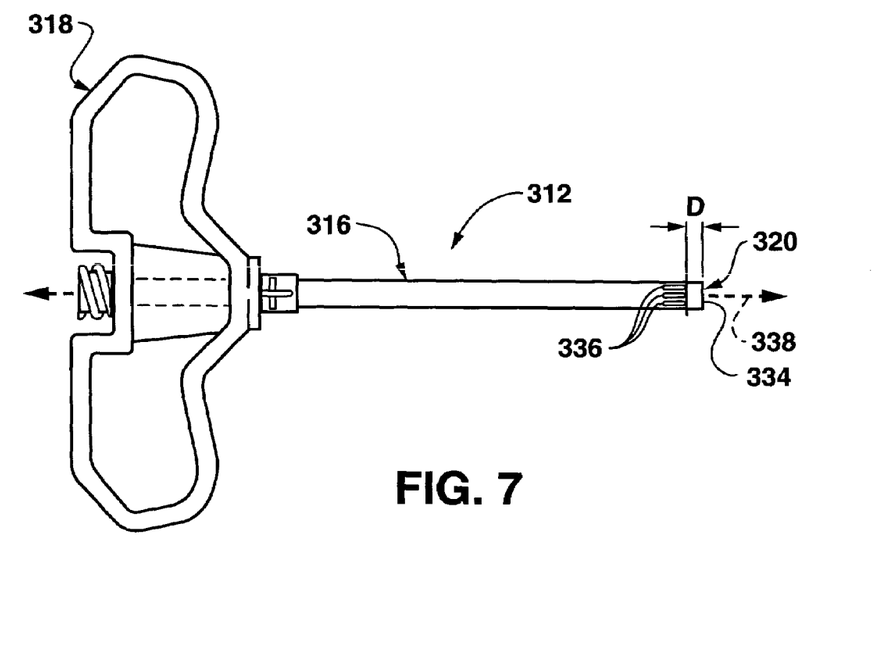
FIG. 7 is a side view of a further alternative bone graft needle according to the present invention.

The bone graft needle 312 illustrated in FIG. 7 is representative of a delivery member 316 having radial ports 336 that are not circular in perimetrical configuration. The radial ports 336 are formed as elongate slots in delivery member 316, and the slots begin a distance D proximally of the circumferential edge 334, which is disposed in a plane perpendicular to central longitudinal axis 338.

Figure 8:
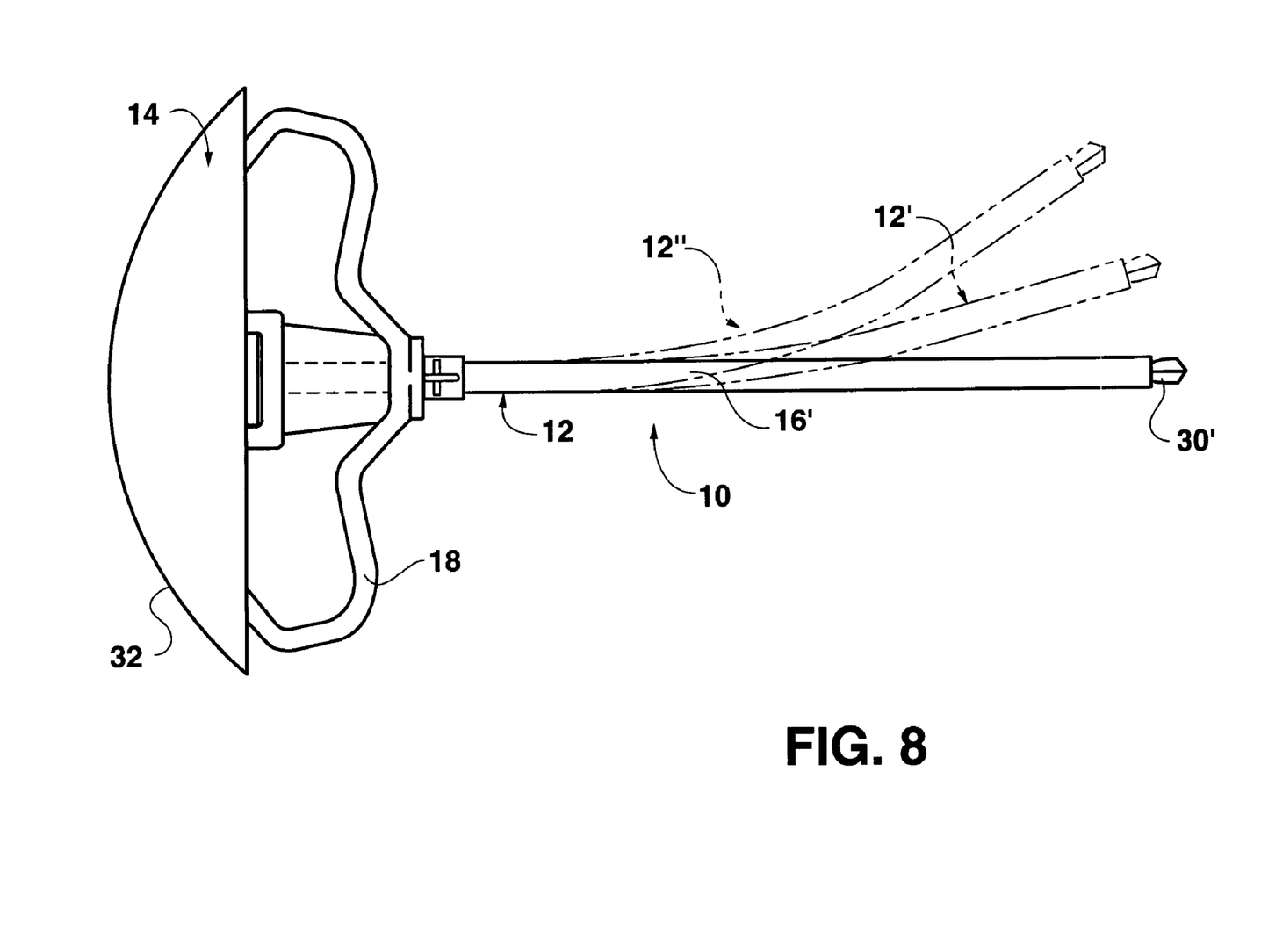
FIG. 8 is a side view of an instrument assembly according to the present invention, in which the instrument assembly is bendable.

FIG. 8 shows an alternative embodiment of an instrument assembly 10 according to the invention. As with the main embodiment of the invention, instrument assembly 10 comprises a bone graft needle 12 and a penetrating member 14, such as a trocar. While the bone graft needle 12 is shown as not having radial ports 36, that is because radial ports are not important to this aspect of the invention and may be omitted.

However, in this embodiment, both bone graft needle 12 and penetrating member 14 are constructed so as to be easily bendable with minimal crimping (to not impede fluid flow there through), yet not easily break. This allows the user to bend the combined instrument 10 into any number of curved shapes that ultimately allow the bone graft needle 12', 12" to more easily access hard to reach areas of the body.

An exemplary construction of bone graft needle 12 so that it is easily bendable with minimal crimping, yet not easily break is forming tubular delivery member 16' out of thin-walled stainless steel, of approximately 6–11 gauge.

Figure 10:
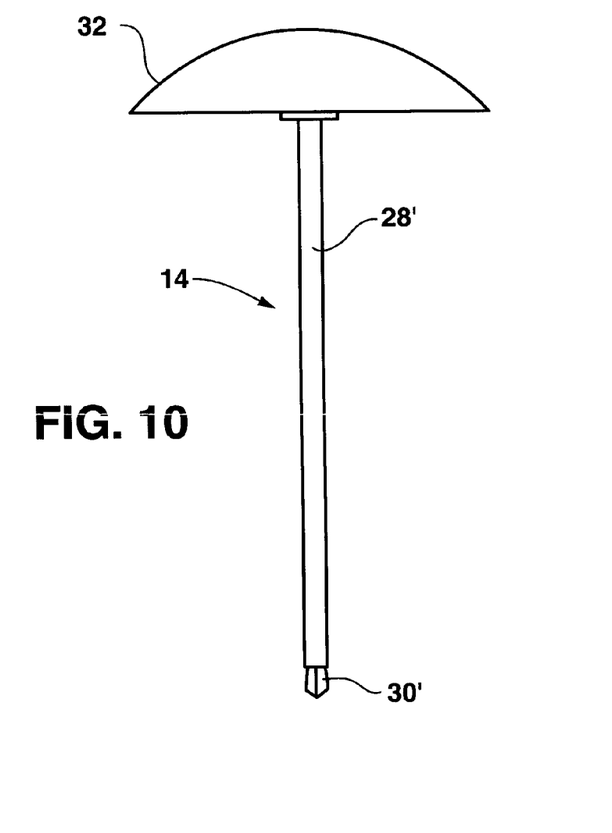
FIG. 10 depicts an exemplary construction of bendable penetrating member 14 for use with the invention.

An exemplary construction of penetrating member 14 so that it is easily bendable with minimal crimping, yet not easily break is shown in FIG. 10. This exemplary construction comprises forming elongate shaft 28' out of either solid or hollow PolyEtherEtherKetone (PEEK), with a stainless steel tip 30' for body member penetrating ability. Penetrating member 14 must be flexible enough to allow for removal from the needle 12 after the needle 12 has been bent.

Figure 9:
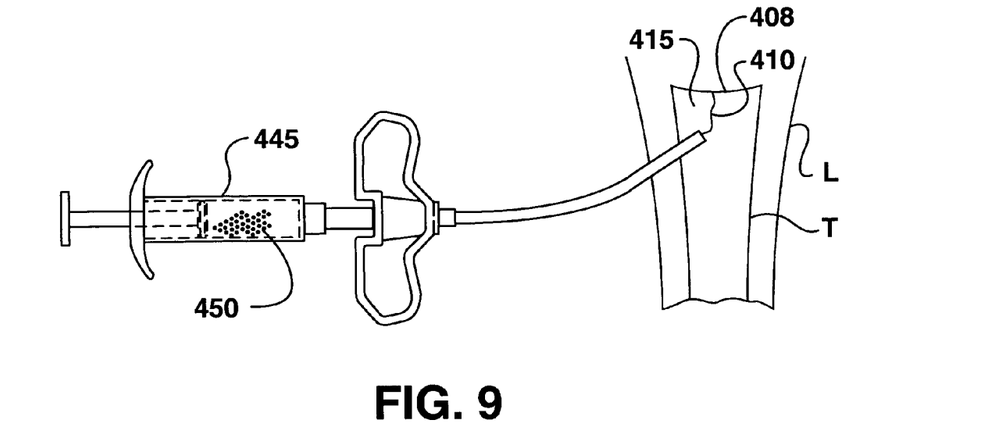
FIG. 9 shows an exemplary, use of the alternative instrument assembly of FIG. 8.

One hard to reach area in which this aspect of the invention is useful, is the tibial plateau 400, such as shown in FIG. 9. Tibial plateau 400 is shown as having a fracture 410 that results in a small bone fragment 415 that needs to be secured in position.

A doctor, after reviewing x-rays or by any other known method, can judge the best instrument 10 approach for introducing bone graft material to the fracture area. Then, intra-operatively, the doctor can bend instrument 10 to the desired curvature, by either matching it to a template or by trial and error based upon experience. Penetrating member 14 will preferably be positioned within bone graft needle 12 during the bending process to assure a matching curvature between the two components. Any device or method can be used for bending instrument 10, for example, that shown in U.S. Pat. No. 6,368,335, whose contents are incorporated by reference herein.

The instrument 10 is inserted into the lower leg L and tibia T and the tip of the instrument brought next to the fracture 410. Penetrating member 14 is then removed from bone graft needle 12. Syringe 445, filled with bone graft material 450 is connected to bone graft needle 12 via conventional methods, and pumped into the fracture site, as previously described.

Inasmuch as the present invention is subject to many variations, modifications and changes in detail, it is intended that all subject matter discussed above or shown in the accompanying drawings be interpreted as illustrative only and not be taken in a limiting sense.

What is claimed is:

1. A method of delivering bone graft material to a bone defect area in a patient's body through a minimally invasive portal, comprising:

providing an instrument assembly for delivering the bone graft material to the bone defect area, said instrument assembly comprising:

a bone graft needle for delivery of bone graft material to the bone defect area, said needle comprising an elongate bendable tubular delivery member having an open distal end for positioning at the bone defect area via the minimally invasive portal providing access to the bone defect area from externally of the patient's body and having an open proximal end for being supplied with bone graft material from externally of the patient's body, said open distal end being aligned with a central longitudinal axis of said delivery member for discharge of the bone graft material therefrom towards the bone defect area; and an elongate flexible penetrating member for receipt within said bone graft needle, inserting said elongate flexible penetrating member into said bone graft needle until a distal end of said elongate flexible penetrating member extends from said open distal end of said bone graft needle, bending said instrument assembly intraoperatively while said elongate flexible penetrating member is inserted in said bone graft needle to thereby provide said bone graft needle with a selected bent configuration, said selected bent configuration configured for accessing the bone defect area, inserting said instrument assembly having said selected bent configuration through the minimally invasive portal until said distal end of said bone graft needle operatively reaches the bone defect area, while maintaining said proximal end of said bone graft needle external of the patient's body, removing said elongate flexible penetrating member from said bone graft needle while retaining said distal end of said bone graft needle at said bone defect area, said elongate flexible penetrating member being sufficiently flexible to allow said elongate flexible penetrating member to be removed from said bone graft needle without substantially altering said selected bent configuration of said bone graft needle, and delivering a bone graft material in paste form to the bone defect area via injection of said bone graft material through said bone graft needle, said bone graft material comprising calcium sulfate.

2. The method of claim 1, wherein both said bone graft needle and said elongate flexible penetrating member are constructed so as to be easily bendable with minimal crimping so as not to impede fluid flow through said bone graft needle, yet not easily break.

3. The method of claim 2, wherein said bone graft needle and said penetrating member are configured to allow bending the instrument assembly into any number of curved shapes that allow the bone graft needle to more easily access hard to reach bone defect areas of the patient's body.

4. The method of claim 3, wherein said elongate flexible penetrating member is formed of polyether-ether-ketone and has a stainless steel tip.

5. The method of claim 2, wherein said tubular delivery member is formed of thin-walled stainless steel of about 6 to about 11 gauge.

6. The method of claim 1, wherein said instrument assembly is bent to said selected bent configuration by matching said instrument assembly to a template.

7. The method of claim 1, wherein said instrument assembly is bent to said selected bent configuration using a cannula bender, said cannula bender configured for use in bending said bone graft needle without kinking said bone graft needle.

8. The method of claim 7, wherein said cannula bender is configured for use in bending said bone graft needle along various radii of curvature.

9. The method of claim 8, wherein said cannula bender is configured for use in bending said bone graft needle in more than one plane.

10. The method of claim 1, wherein said bone graft material includes demineralized bone matrix.

* * * * *